(12) United States Patent
Wilkinson et al.

(10) Patent No.: US 11,974,846 B2
(45) Date of Patent: *May 7, 2024

(54) BIOLOGICAL FLUID TRANSFER DEVICE AND BIOLOGICAL FLUID SAMPLING SYSTEM

(71) Applicant: Becton, Dickinson and Company, Franklin Lakes, NJ (US)

(72) Inventors: Bradley M. Wilkinson, North Haledon, NJ (US); Daniel J. Marchiarullo, Morris Plains, NJ (US); Gary D. Fletcher, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 117 days.

This patent is subject to a terminal disclaimer.

(21) Appl. No.: 17/007,875

(22) Filed: Aug. 31, 2020

(65) Prior Publication Data

US 2020/0397359 A1 Dec. 24, 2020

Related U.S. Application Data

(63) Continuation of application No. 16/425,015, filed on May 29, 2019, now Pat. No. 10,791,975, which is a (Continued)

(51) Int. Cl.
*A61B 5/15* (2006.01)
*A61B 5/151* (2006.01)
(Continued)

(52) U.S. Cl.
CPC ...... *A61B 5/150213* (2013.01); *A61B 5/1411* (2013.01); *A61B 5/150022* (2013.01);
(Continued)

(58) Field of Classification Search
None
See application file for complete search history.

(56) References Cited

U.S. PATENT DOCUMENTS 3,159,159 A 12/1964 Cohen
3,322,114 A 5/1967 Portnoy et al.
(Continued)

FOREIGN PATENT DOCUMENTS

CN 1169886 A 1/1998
CN 1262606 A 8/2000
(Continued)

OTHER PUBLICATIONS

Amasia et al., "Large-volume centrifugal microfluidic device for blood plasma separation", Bioanalysis, 2010, pp. 1701-1710, vol. 2:10.
(Continued)

*Primary Examiner* — Lore R Jarrett
(74) *Attorney, Agent, or Firm* — The Webb Law Firm

(57) ABSTRACT

A biological fluid sampling transfer device adapted to receive a multi-component blood sample is disclosed. After collecting the blood sample, the biological fluid sampling transfer device is able to separate a plasma portion from a cellular portion. After separation, the biological fluid sampling transfer device is able to transfer the plasma portion of the blood sample to a point-of-care testing device. The biological fluid sampling transfer device also provides a closed sampling and transfer system that reduces the exposure of a blood sample and provides fast mixing of a blood sample with a sample stabilizer. The biological fluid sampling transfer device is engageable with a blood testing device for closed transfer of a portion of the plasma portion from the biological fluid sampling transfer device to the blood testing device. The blood testing device is adapted to
(Continued)

receive the plasma portion to analyze the blood sample and obtain test results.

12 Claims, 8 Drawing Sheets

Related U.S. Application Data continuation of application No. 14/251,681, filed on Apr. 14, 2014, now Pat. No. 10,342,471.

(60) Provisional application No. 61/811,918, filed on Apr. 15, 2013.

(51) Int. Cl.
    *A61B 5/157*     (2006.01)
    *A61M 1/34*     (2006.01)
    *A61M 1/36*     (2006.01)
    *B01L 3/00*     (2006.01)
    *B04B 7/08*     (2006.01)
    *G01N 1/28*     (2006.01)
    *G01N 1/34*     (2006.01)
    *G01N 1/40*     (2006.01)
    *G01N 33/49*     (2006.01)

(52) U.S. Cl.
CPC .... *A61B 5/15003* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150442* (2013.01); *A61B 5/150748* (2013.01); *A61B 5/150755* (2013.01); *A61B 5/150778* (2013.01); *A61B 5/151* (2013.01); *A61B 5/15101* (2013.01); *A61B 5/15105* (2013.01); *A61B 5/15144* (2013.01); *A61B 5/15198* (2013.01); *A61B 5/157* (2013.01); *A61M 1/34* (2013.01); *A61M 1/3406* (2014.02); *A61M 1/36* (2013.01); *B01L 3/502* (2013.01); *B01L 3/5021* (2013.01); *B01L 3/50273* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150969* (2013.01); *B01L 2200/027* (2013.01); *B01L 2200/0621* (2013.01); *B01L 2200/0631* (2013.01); *B01L 2200/0684* (2013.01); *B01L 2200/10* (2013.01); *B01L 2300/0627* (2013.01); *B01L 2300/0672* (2013.01); *B01L 2300/0681* (2013.01); *B01L 2300/0803* (2013.01); *B01L 2300/0864* (2013.01); *B01L 2300/0877* (2013.01); *B01L 2400/0406* (2013.01); *B01L 2400/0409* (2013.01); *B01L 2400/0478* (2013.01); *B01L 2400/0688* (2013.01); *G01N 2001/4016* (2013.01); *G01N 2001/4088* (2013.01)

(56) References Cited

U.S. PATENT DOCUMENTS

| | | | |
|---|---|---|---|
| 3,640,393 A | 2/1972 | Hurtig | |
| 3,848,579 A | 11/1974 | Villa-Real | |
| 4,134,512 A | 1/1979 | Nugent | |
| 4,146,172 A | 3/1979 | Cullis et al. | |
| 4,436,098 A | 3/1984 | Kaufman | |
| 4,511,349 A | 4/1985 | Nielsen et al. | |
| 4,627,445 A | 12/1986 | Garcia et al. | |
| 4,842,591 A | 6/1989 | Luther | |
| 4,999,304 A | 3/1991 | Robertson | |
| 5,055,203 A | 10/1991 | Columbus | |
| 5,160,702 A | 11/1992 | Kopf-Sill et al. | |
| 5,163,442 A | 11/1992 | Ono | |
| 5,219,999 A | 6/1993 | Suzuki et al. | |
| 5,242,606 A | 9/1993 | Braynin et al. | |
| 5,304,348 A | 4/1994 | Burd et al. | |
| 5,364,533 A * | 11/1994 | Ogura | A61B 5/154 210/504 |
| 5,422,018 A | 6/1995 | Saunders et al. | |
| 5,578,459 A * | 11/1996 | Gordon | B01L 3/5025 210/651 |
| 5,636,640 A | 6/1997 | Staehlin | |
| 5,638,828 A | 6/1997 | Lauks et al. | |
| 5,657,963 A | 8/1997 | Hinchliffe et al. | |
| 5,690,618 A | 11/1997 | Smith et al. | |
| 5,726,026 A | 3/1998 | Wilding et al. | |
| 5,733,446 A | 3/1998 | Holm | |
| 5,839,715 A | 11/1998 | Leinsing | |
| 5,879,624 A | 3/1999 | Boehringer et al. | |
| 5,922,591 A | 7/1999 | Anderson et al. | |
| 5,979,669 A | 11/1999 | Kitajima et al. | |
| 6,063,039 A | 5/2000 | Cunningham et al. | |
| 6,074,183 A | 6/2000 | Allen et al. | |
| 6,170,671 B1 | 1/2001 | Kitajima et al. | |
| 6,264,619 B1 | 7/2001 | Ferguson | |
| 6,372,182 B1 | 4/2002 | Mauro et al. | |
| 6,506,167 B1 | 1/2003 | Ishimito et al. | |
| 6,537,242 B1 | 3/2003 | Palmer | |
| 6,613,064 B2 | 9/2003 | Rutynowski et al. | |
| 6,869,405 B2 | 3/2005 | Marsden | |
| 7,001,344 B2 | 2/2006 | Freeman et al. | |
| 7,014,625 B2 | 3/2006 | Bengtsson | |
| 7,378,259 B2 | 5/2008 | Bahatt et al. | |
| 7,678,580 B2 | 3/2010 | Kuriger | |
| 7,803,123 B2 | 9/2010 | Perez et al. | |
| 8,075,496 B2 | 12/2011 | Deck et al. | |
| 8,114,351 B2 | 2/2012 | Degenhardt | |
| 8,158,410 B2 | 4/2012 | Tang et al. | |
| 8,163,253 B1 | 4/2012 | Hartselle | |
| 8,211,036 B2 | 7/2012 | Schraga | |
| 8,267,911 B2 | 9/2012 | Gallogly et al. | |
| 8,328,735 B2 | 12/2012 | Haar et al. | |
| 8,383,044 B2 | 2/2013 | Davis et al. | |
| 8,469,984 B2 | 6/2013 | Ruan et al. | |
| 8,470,588 B2 | 6/2013 | Boehm et al. | |
| 8,491,499 B2 | 7/2013 | Choi et al. | |
| 8,491,840 B2 | 7/2013 | Cho et al. | |
| 8,764,657 B2 | 7/2014 | Curry et al. | |
| 9,028,425 B2 | 5/2015 | Burkholz | |
| 9,119,578 B2 | 9/2015 | Haghgooie et al. | |
| 9,295,417 B2 | 3/2016 | Haghgooie et al. | |
| 9,404,075 B2 * | 8/2016 | Pflanz | C12M 47/02 |
| 9,517,026 B2 | 12/2016 | Gelfand et al. | |
| 9,549,700 B2 | 1/2017 | Fletcher et al. | |
| 9,549,701 B2 | 1/2017 | Peterson et al. | |
| 2002/0009015 A1 | 1/2002 | Laugharn, Jr. et al. | |
| 2002/0143298 A1 | 10/2002 | Marsden | |
| 2003/0013205 A1 | 1/2003 | Konrad | |
| 2003/0134416 A1 | 7/2003 | Yamanishi et al. | |
| 2003/0232712 A1 | 12/2003 | Dolecek et al. | |
| 2004/0069459 A1 | 4/2004 | Tonosaki et al. | |
| 2004/0116830 A1 | 6/2004 | Trudeau et al. | |
| 2004/0142463 A1 | 7/2004 | Walker et al. | |
| 2004/0142493 A1 | 7/2004 | Hutchens et al. | |
| 2004/0143226 A1 | 7/2004 | Marsden | |
| 2004/0230216 A1 | 11/2004 | Levaughn et al. | |
| 2004/0252584 A1 * | 12/2004 | Ji | B01F 25/4331 366/338 |
| 2005/0004494 A1 * | 1/2005 | Perez | A61B 5/150358 600/583 |
| 2005/0015020 A1 | 1/2005 | Levaughn et al. | |
| 2005/0026301 A1 | 2/2005 | Petithory | |
| 2005/0133439 A1 | 6/2005 | Blickhan | |
| 2005/0139547 A1 | 6/2005 | Manoussakis et al. | |
| 2005/0196872 A1 | 9/2005 | Nguyen et al. | |
| 2005/0214927 A1 | 9/2005 | Haley | |
| 2005/0273019 A1 | 12/2005 | Conway et al. | |

(56) References Cited

U.S. PATENT DOCUMENTS

| | | |
|---|---|---|
| 2006/0009713 A1 | 1/2006 | Flaherty |
| 2006/0029923 A1 | 2/2006 | Togawa et al. |
| 2006/0127277 A1 | 6/2006 | Numajiri |
| 2006/0160243 A1 | 7/2006 | Tang et al. |
| 2006/0228258 A1 | 10/2006 | Samsoondar |
| 2006/0228259 A1 | 10/2006 | Samsoondar |
| 2006/0229530 A1 | 10/2006 | Hosoda et al. |
| 2006/0240964 A1 | 10/2006 | Lolachi et al. |
| 2007/0031283 A1 | 2/2007 | Davis et al. |
| 2007/0160503 A1 | 7/2007 | Sethu et al. |
| 2007/0265549 A1 | 11/2007 | Channer et al. |
| 2008/0097315 A1 | 4/2008 | Miner et al. |
| 2008/0135502 A1 | 6/2008 | Pyo et al. |
| 2008/0176068 A1 | 7/2008 | Neubert et al. |
| 2008/0240990 A1 | 10/2008 | Flaherty |
| 2008/0287906 A1 | 11/2008 | Burkholz et al. |
| 2009/0004060 A1 | 1/2009 | Omuro et al. |
| 2009/0105614 A1 | 4/2009 | Momose et al. |
| 2009/0120865 A1 | 5/2009 | Chung et al. |
| 2009/0136982 A1 | 5/2009 | Tang et al. |
| 2009/0181411 A1 | 7/2009 | Battrell et al. |
| 2009/0204026 A1 | 8/2009 | Crawford et al. |
| 2009/0281525 A1 | 11/2009 | Harding et al. |
| 2009/0286309 A1 | 11/2009 | Roderfeld |
| 2010/0021910 A1* | 1/2010 | Cao .................. C12N 15/1017 435/270 |
| 2010/0089815 A1 | 4/2010 | Zhang et al. |
| 2010/0093551 A1 | 4/2010 | Montagu |
| 2010/0198108 A1 | 8/2010 | Alden |
| 2010/0241031 A1 | 9/2010 | Lai |
| 2011/0009717 A1 | 1/2011 | Davis et al. |
| 2011/0058985 A1 | 3/2011 | Saiki et al. |
| 2011/0092784 A1 | 4/2011 | Butler et al. |
| 2011/0124130 A1 | 5/2011 | Wagner et al. |
| 2011/0124984 A1 | 5/2011 | Rostaing |
| 2011/0134426 A1 | 6/2011 | Kaduchak et al. |
| 2011/0263030 A1 | 10/2011 | Kim |
| 2012/0016213 A1 | 1/2012 | Burkholz |
| 2012/0134974 A1 | 5/2012 | Sehgal |
| 2012/0152858 A1 | 6/2012 | Yang |
| 2012/0275955 A1 | 11/2012 | Haghgooie et al. |
| 2012/0277696 A1 | 11/2012 | Gonzalez-Zugasti et al. |
| 2012/0277697 A1 | 11/2012 | Haghgooie et al. |
| 2013/0026085 A1 | 1/2013 | Samsoondar |
| 2013/0040333 A1 | 2/2013 | Karlsson |
| 2013/0052675 A1 | 2/2013 | Karlsson et al. |
| 2013/0082012 A1 | 4/2013 | Lean et al. |
| 2013/0086980 A1 | 4/2013 | Gadini et al. |
| 2013/0165867 A1 | 6/2013 | Isaacson et al. |
| 2013/0175213 A1 | 7/2013 | Dorrer et al. |
| 2013/0209331 A1 | 8/2013 | Rodenfels et al. |

FOREIGN PATENT DOCUMENTS

| | | |
|---|---|---|
| CN | 1382966 A | 12/2002 |
| CN | 1525834 A | 9/2004 |
| CN | 1846603 A | 10/2006 |
| CN | 1929782 A | 3/2007 |
| CN | 1993079 A | 7/2007 |
| CN | 101102847 A | 1/2008 |
| CN | 101288592 A | 10/2008 |
| CN | 101317758 A | 12/2008 |
| CN | 101332320 A | 12/2008 |
| CN | 101600963 A | 12/2009 |
| CN | 101695446 A | 4/2010 |
| CN | 102429665 A | 5/2012 |
| CN | 102573629 A | 7/2012 |
| CN | 102764133 A | 11/2012 |
| CN | 202714857 U | 2/2013 |
| CN | 202844313 U | 4/2013 |
| DE | 202008010918 U1 | 12/2008 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 51162582 | 6/1950 |
| JP | S544191 | 1/1979 |
| JP | H01297159 A | 11/1989 |
| JP | H0275332 A | 3/1990 |
| JP | H04276258 A | 10/1992 |
| JP | H07500910 A | 1/1995 |
| JP | H07503794 A | 4/1995 |
| JP | 200074908 A | 3/2000 |
| JP | 200319126 A | 1/2003 |
| JP | 2004150891 A | 5/2004 |
| JP | 2004354387 A | 12/2004 |
| JP | 2004361419 A | 12/2004 |
| JP | 2005270729 A | 10/2005 |
| JP | 2005287955 A | 10/2005 |
| JP | 2005349195 A | 12/2005 |
| JP | 200668384 A | 3/2006 |
| JP | 2006214955 A | 8/2006 |
| JP | 2006218447 A | 8/2006 |
| JP | 200750100 A | 3/2007 |
| JP | 2007249306 A | 9/2007 |
| JP | 2007315879 A | 12/2007 |
| JP | 2008157960 A | 7/2008 |
| JP | 2008302077 A | 12/2008 |
| JP | 2009128367 A | 6/2009 |
| JP | 2009264858 A | 11/2009 |
| JP | 2010505096 A | 2/2010 |
| JP | 2010146123 A | 7/2010 |
| JP | 2010147371 A | 7/2010 |
| JP | 2010237050 A | 10/2010 |
| JP | 201155916 A | 3/2011 |
| JP | 2012530256 A | 11/2012 |
| JP | 2012532683 A | 12/2012 |
| JP | 2013518276 A | 5/2013 |
| JP | 5508709 B2 | 6/2014 |
| KR | 1020100007809 A | 1/2010 |
| WO | 9118656 A1 | 12/1991 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2011093602 A2 | 8/2011 |
| WO | 2012121686 A1 | 9/2012 |

OTHER PUBLICATIONS

Lee, "A fully automated immunoassay from whole blood on a disc", Lab Chip, 2009, pp. 1548-1555, vol. 9.

Membrane Separation Technology for Research and Quality Control, Sartorius AG, Separation Technology, Laboratory Filtration, Mar. 1, 1997.

Zehnle, "Centrifugo-dynamic inward pumping of liquids on a centrifugal micofluidic platform", 2012, Royal Society of Chemistry, Lab Chip, pp. 5142-5145, vol. 12.

\* cited by examiner

BIOLOGICAL FLUID TRANSFER DEVICE AND BIOLOGICAL FLUID SAMPLING SYSTEM

CROSS REFERENCE TO RELATED APPLICATIONS

The present application is a continuation of U.S. application Ser. No. 16/425,015, filed May 29, 2019, entitled "Biological Fluid Transfer Device and Biological Fluid Sampling System", which is a continuation of U.S. application Ser. No. 14/251,681, filed Apr. 14, 2014, entitled "Biological Fluid Transfer Device and Biological Fluid Sampling System" (now U.S. Pat. No. 10,342,471), which claims priority to U.S. Provisional Application No. 61/811,918, filed Apr. 15, 2013, entitled "Medical Device for Collection of a Biological Sample", the entire disclosures of each of which are hereby incorporated by reference in their entirety.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid sampling transfer device, such as a blood sampling transfer device that is adapted to receive a blood sample having a cellular portion and a plasma portion. After collecting the blood sample, the blood sampling transfer device is able to separate the plasma portion from the cellular portion. After separation, the blood sampling transfer device is able to transfer the plasma portion of the blood sample to a point-of-care testing device. The blood sampling transfer device of the present disclosure also provides a closed sampling and transfer system that reduces the exposure of a blood sample and provides fast mixing of a blood sample with a sample stabilizer. The sample stabilizer can be an anticoagulant, or a substance designed to preserve a specific element within the blood such as, for example, RNA, protein analyte, or other element. The blood sampling transfer device is engageable with a blood testing device for closed transfer of a portion of the plasma portion from the blood sampling transfer device to the blood testing device. The blood testing device is adapted to receive the plasma portion to analyze the blood sample and obtain test results.

Some of the advantages of the blood sampling transfer device and the biological fluid separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood sampling transfer device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

In accordance with an embodiment of the present invention, a biological fluid transfer device adapted to receive a multi-component blood sample includes a housing having an inlet port and a transfer port, with the inlet port and the transfer port in fluid communication. The device also includes a mixing channel in fluid communication with the inlet port and the transfer port and shaped to promote mixing of the multi-component blood sample, and a blood separation element disposed between the inlet port and the transfer port. The blood separation element is adapted to restrain a first component of the multi-component blood sample and allow a second component of the multi-component blood sample to pass therethrough.

In one configuration, the first component is a cellular portion of the multi-component blood sample and the second component is a plasma portion of the multi-component blood sample. The mixing channel may include a sample stabilizer. In certain configurations, the inlet port is adapted to receive the multi-component blood sample via connection to a blood collection set. In other configurations, the inlet port is adapted to receive the multi-component blood sample via connection to a capillary device. In still other configurations, the inlet port is adapted to receive the multi-component blood sample via connection to a needle device. In still another configuration, the inlet port is adapted to receive the multi-component blood sample via connection to an intravenous line.

Optionally, the device may also include a wicking membrane adapted to cause the multi-component blood sample to flow into the biological fluid transfer device. The transfer port may include a bellows and a septum transitionable between a closed position and an open position, wherein compression of the bellows actuates the septum from the closed position to the open position. The mixing channel may include a sample stabilizer and the biological fluid transfer device may be a plasma preparation cartridge.

In accordance with another embodiment of the present invention, a biological fluid sampling system, such as a blood sampling system, includes a biological fluid transfer device adapted to receive a multi-component blood sample. The biological fluid transfer device includes a housing having an inlet port and a transfer port, with the inlet port and the transfer port in fluid communication. The device also includes a mixing channel in fluid communication with the inlet port and the transfer port and shaped to promote mixing of the blood sample, and a separation element disposed between the inlet port and the transfer port. The separation element is adapted to restrain a first component of the multi-component blood sample and allow a second component of the multi-component blood sample to pass therethrough. The system also includes a first interface removably connectable to the biological fluid transfer device, the first interface being adapted for connection to a first blood collection device. The system further includes a second interface removably connectable to the biological fluid transfer device, with the second interface being adapted for connection to a second blood collection device. The system also includes a packaging member having a compartment sized and adapted to receive the biological fluid transfer device, the first interface, and the second interface therein.

In certain configurations, the first component is a cellular portion of the multi-component blood sample and the second component is a plasma portion of the multi-component blood sample. The mixing channel may include a sample stabilizer. The inlet port may be adapted to receive the multi-component blood sample via a blood collection set. In other configurations, the inlet port may be adapted to receive the multi-component blood sample via an intravenous line. In other configurations, the inlet port may be adapted to receive the multi-component blood sample via a capillary device. In still other configurations, the inlet port may be adapted to receive the multi-component blood sample via connection to a needle device.

The device may also include a wicking membrane adapted to cause the multi-component blood sample to flow into the biological fluid sampling transfer device. The transfer port may include a bellows and a septum transitionable between a closed position and an open position, wherein compression of the bellows actuates the septum from the closed position to the open position. In certain configurations, the mixing channel includes a sample stabilizer and the biological fluid transfer device is a plasma preparation cartridge. Optionally, the first interface includes a spinlock interface. In another configuration, the second interface includes a capillary interface. In yet another configuration, the packaging member includes a blister package.

In accordance with yet another embodiment of the present invention, a biological fluid separation and testing system for a multi-component blood sample includes a blood sampling transfer device adapted to receive the multi-component blood sample. The blood sampling transfer device includes a housing having an inlet port and a transfer port, with the inlet port and the transfer port in fluid communication. The device also includes a mixing channel in fluid communication with the inlet port and the transfer port and shaped to promote mixing of the blood sample, and a separation element disposed between the inlet port and the transfer port, the separation element adapted to restrain a first component of the multi-component blood sample and allow a second component of the multi-component blood sample to pass therethrough. The system also includes a blood testing device having a receiving port adapted to receive the transfer port of the blood sampling transfer device for closed transfer of at least a portion of the second component from the blood sampling transfer device to the blood testing device.

In certain configurations, the first component is a cellular portion of the multi-component blood sample and the second component is a plasma portion of the multi-component blood sample. The mixing channel may include a sample stabilizer.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
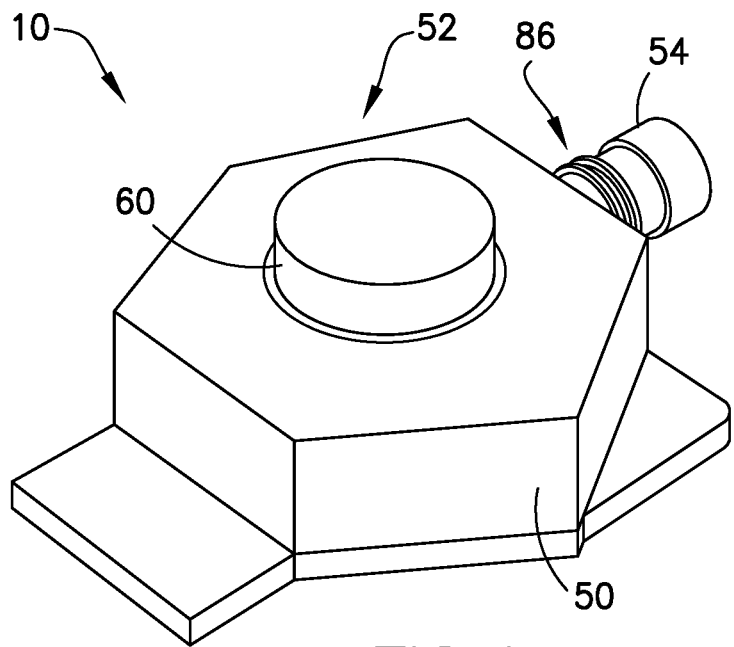
FIG. 1 is a perspective view of a biological fluid sampling transfer device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

FIGS. 1-11 illustrate an exemplary embodiment of the present disclosure. Referring to FIGS. 1-11, a biological fluid sampling transfer device or biological fluid transfer device, such as a blood sampling transfer device or blood transfer device 10 of the present disclosure is adapted to receive a blood sample 12 having a cellular portion 14 and a plasma portion 16. After collecting the blood sample 12, the blood transfer device 10 is able to separate the plasma portion 16 from the cellular portion 14. After separation, the blood transfer device 10 is able to transfer the plasma portion 16 of the blood sample 12 to a point-of-care testing device. The blood transfer device 10 of the present disclosure also provides a closed separation system that reduces the exposure of a blood sample and provides fast mixing of a blood sample with a sample stabilizer.

Figure 2:
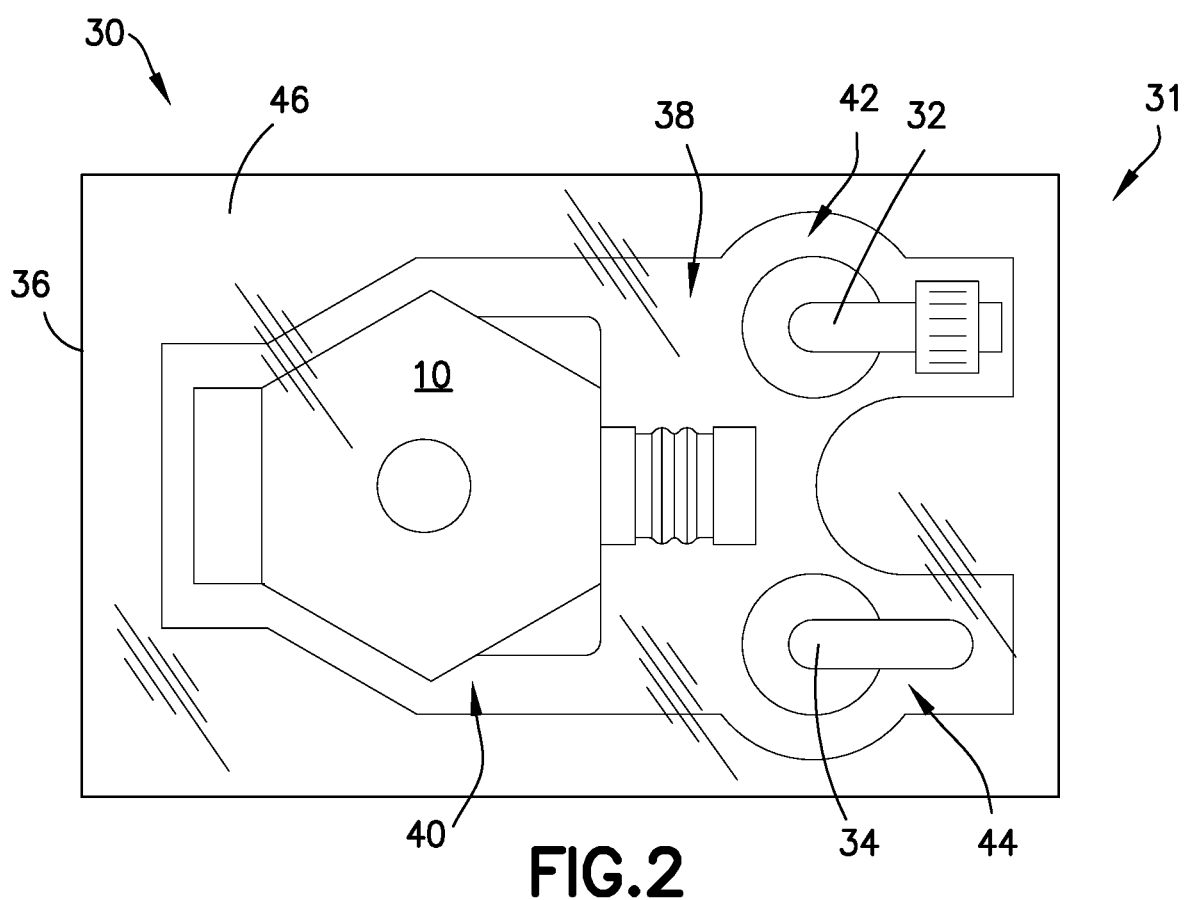
FIG. 2 is an elevation view of a biological fluid sampling system in accordance with an embodiment of the present invention.

FIG. 2 illustrates an exemplary embodiment of the present disclosure. Referring to FIG. 2, a biological fluid sampling system, such as a blood sampling system 30 of the present disclosure includes a kit 31 having a blood sampling transfer device 10, a first interface 32 removably connectable to the blood sampling transfer device 10, the first interface 32 adapted for connection to a first blood collection device, a second interface 34 removably connectable to the blood sampling transfer device 10, the second interface 34 adapted for connection to a second blood collection device, and a packaging member 36 having a compartment 38 sized and adapted to receive the blood sampling transfer device 10, the first interface 32, and the second interface 34 therein.

Figure 8:
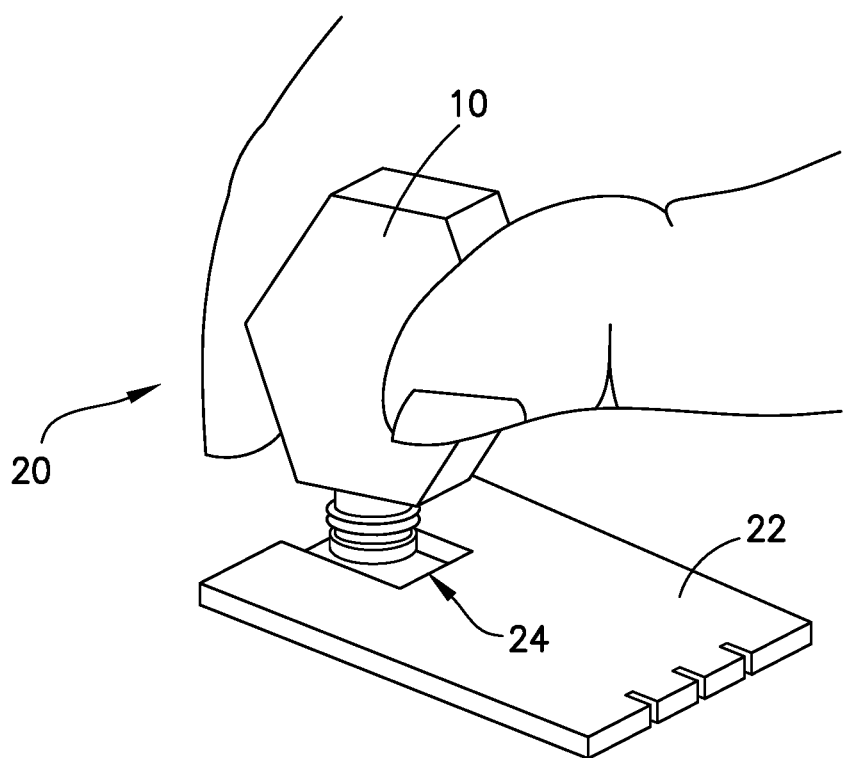
FIG. 8 is a perspective view of a biological fluid sampling transfer device and a point-of-care testing device in accordance with an embodiment of the present invention.

FIG. 8 illustrates an exemplary embodiment of the present disclosure. Referring to FIG. 8, a blood separation and testing system 20 of the present disclosure includes a blood sampling transfer device 10 and a blood testing device or point-of-care testing device 22 engageable with the blood sampling transfer device 10 for closed transfer of a portion of the plasma portion 16 (FIG. 11) from the blood sampling transfer device 10 to the blood testing device 22. The blood testing device 22 is adapted to receive the plasma portion 16 to analyze the blood sample and obtain test results.

Some of the advantages of the blood sampling transfer device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood sampling transfer device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

Referring to FIGS. 1-11, a blood sampling transfer device 10 generally includes a housing 50 having an inlet port 52, an outlet port or transfer port 54 in fluid communication with the inlet port 52, a flow channel or a mixing channel 56 in fluid communication with the inlet port 52 and the transfer port 54, a blood separation element 58 disposed between the inlet port 52 and the transfer port 54, a valve or septum 86 disposed at the transfer port 54, an interface connection portion 60, and an exit channel 68. The interface connection portion 60 allows the first interface 32 or the second interface 34 to be removably connected to the blood sampling transfer device 10 to allow for the collection of a blood sample 12 into the blood sampling transfer device 10.

Referring to FIG. 2, a blood sampling system 30 of the present disclosure includes a kit 31 having a blood sampling transfer device 10, a first interface 32 removably connectable to the blood sampling transfer device 10, the first interface 32 adapted for connection to a first blood collection device, a second interface 34 removably connectable to the blood sampling transfer device 10, the second interface 34 adapted for connection to a second blood collection device, and a packaging member 36 having a compartment 38 sized and adapted to receive the blood sampling transfer device 10, the first interface 32, and the second interface 34 therein.

The packaging member 36 includes a body or wall 46 defining a compartment 38. In one embodiment, the body 46 of the packaging member 36 defines a first compartment 40 sized and adapted to receive the blood sampling transfer device 10 therein, a second compartment 42 sized and adapted to receive the first interface 32 therein, and a third compartment 44 sized and adapted to receive the second interface 34 therein. In one embodiment, the packaging member 36 comprises a blister package. In one embodiment, a sealing cover is secured over the packaging member 36 to seal the blood sampling transfer device 10, the first interface 32, and the second interface 34 therein, i.e., the sealing cover provides a substantially impermeable enclosure with respect to packaging member 36, provides a leak prevention and protection enclosure, protects the contents of the blood sampling transfer device 10 and the interfaces 32, 34 contained within packaging member 36, and/or maintains a sealed, sterilized environment within packaging member 36. The sealing cover of the packaging member 36 provides a sufficient seal at a range of temperatures, pressures, and humidity levels. In one embodiment, tamper evidence is also provided by use of a tear strip or other indicating means secured to a portion of the sealing cover and/or packaging member 36 to indicate tampering with the contents of packaging member 36.

In one embodiment, the blood sampling transfer device 10 is a plasma preparation cartridge. In one embodiment, the first interface 32 is a spinlock interface. In one embodiment, the second interface 34 is a capillary collection interface. In one embodiment, the packaging member 36 is a blister package. The system of the present disclosure allows the blood sampling transfer device 10 to receive a blood sample from a variety of sources including, but not limited to, an integral micro-needle device or lancet device 62 (FIG. 6), a blood collection set 100 (FIG. 3), an intravenous line or PICC line 104 (FIG. 4), a capillary device or needle device 106 (FIG. 5), or a finger-stick capillary bed (not shown).

In one embodiment, there are three primary ways a user can collect blood into the blood sampling transfer device 10. For example, these ways may be as follows: 1) venous blood via venipuncture and connecting to a blood collection set 100 or IV with the first interface 32 and a resealable valve or septum (arterial draws may be accomplished by connecting this interface system to an indwelling line); 2) capillary blood via a capillary stick with a lancet on a finger of the patient with the second interface 34; and 3) venous-like blood by using the micro-needle device 62 to puncture the arm of a patient. This universal approach offers the greatest flexibility in allowing the clinician to determine what is best for the patient under his or her care. In other embodiments, there are additional ways a user can collect blood into the blood sampling transfer device 10.

Figure 3:
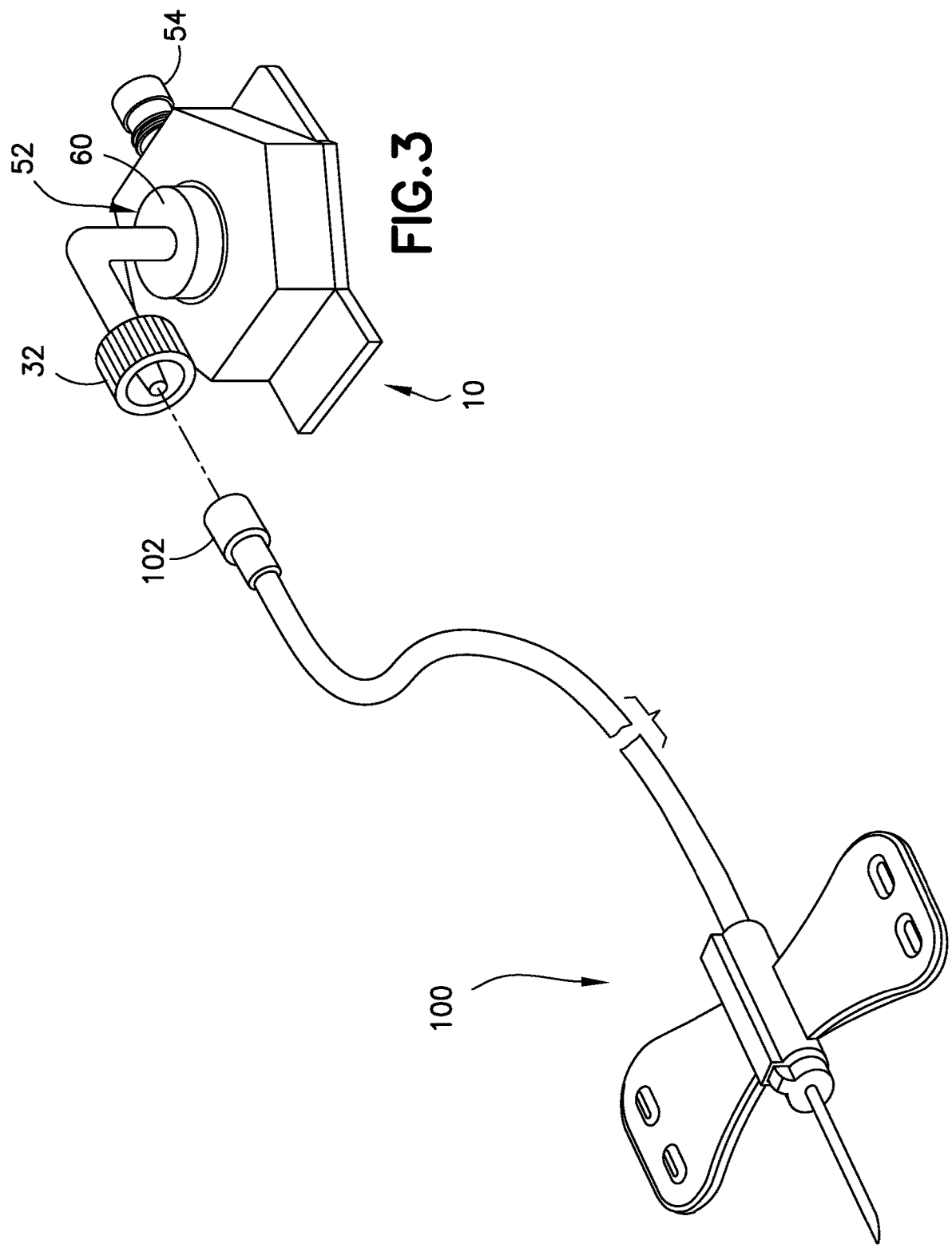
FIG. 3 is a perspective view of a biological fluid sampling transfer device in accordance with an embodiment of the present invention, with a first biological fluid collection device.
Figure 4:
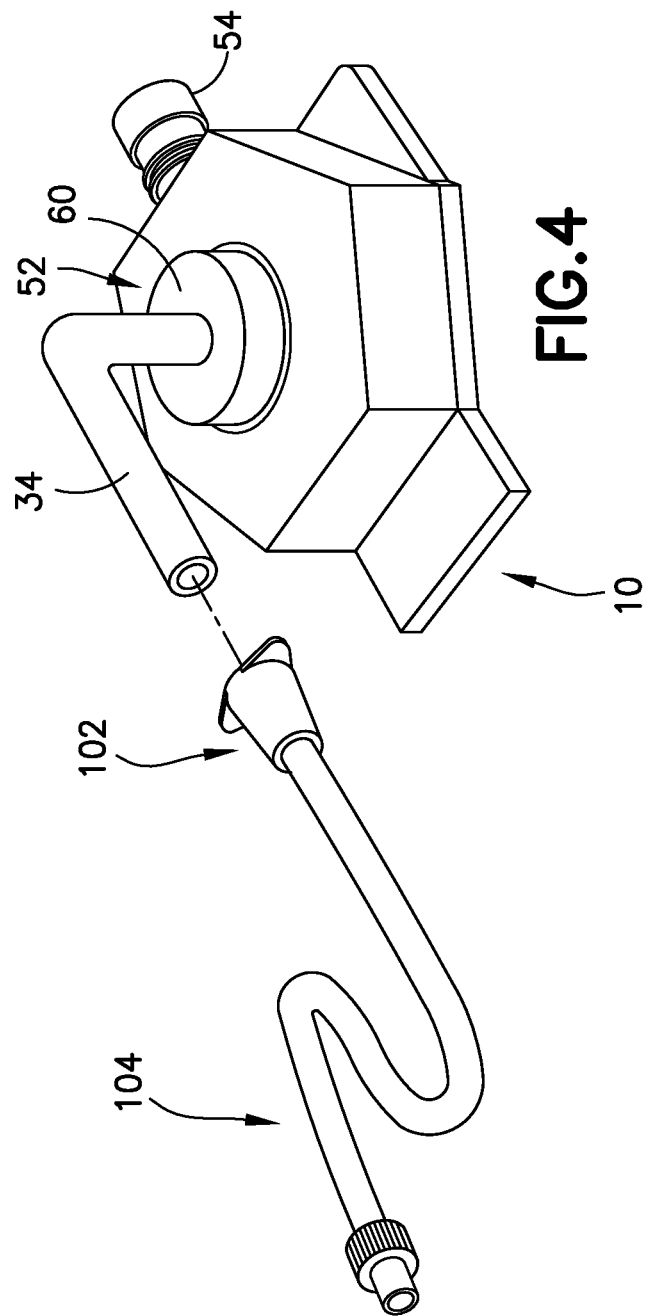
FIG. 4 is a perspective view of a biological fluid sampling transfer device in accordance with an embodiment of the present invention, with a second biological fluid collection device.
Figure 5:
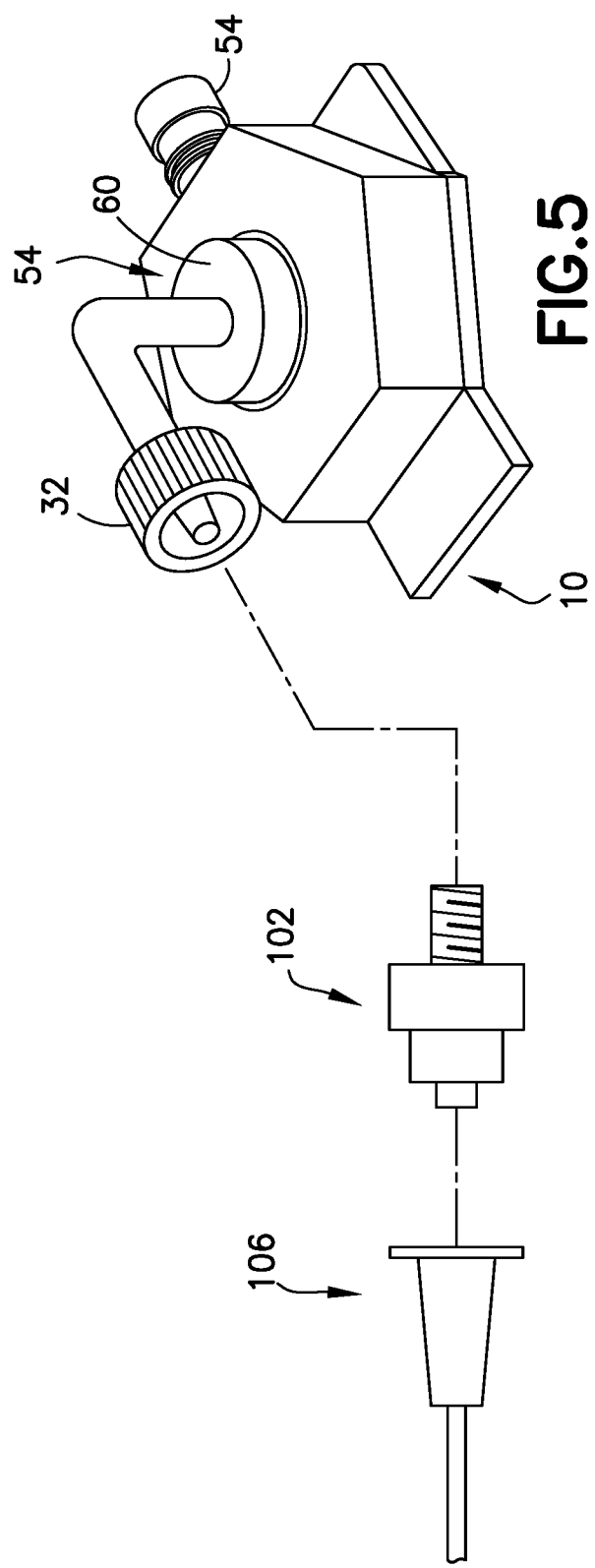
FIG. 5 is a perspective view of a biological fluid sampling transfer device in accordance with an embodiment of the present invention, with a third biological fluid collection device.

Referring to FIG. 3, in one embodiment, the inlet port 52 is adapted to be connected to a blood collection set 100 via the first interface 32 to allow for the collection of a blood sample 12 into the blood sampling transfer device 10. The inlet port 52 may be sized and adapted for engagement with a separate device, such as a needle assembly or IV connection assembly and, therefore, may include a mechanism for such engagement as is conventionally known. For example, in one embodiment, the inlet port 52 may include a luer lock or luer tip for engagement with an optional separate luer mating component of such a separate device for attachment therewith. For example, referring to FIG. 3, the blood collection set 100 may include a luer component 102 for engagement with inlet port 52 of blood sampling transfer device 10. In this manner, the inlet port 52 is connectable to the blood collection set 100 for the collection of a blood sample into the blood sampling transfer device 10. In addition, a mechanism for locking engagement between the inlet port 52 and the blood collection set 100 may also be provided. Such luer connections and luer locking mechanisms are well known in the art. The blood collection set 100 may include a needle assembly, an IV connection assembly, a PICC line, an arterial indwelling line, or similar blood collection means.

Figure 7:
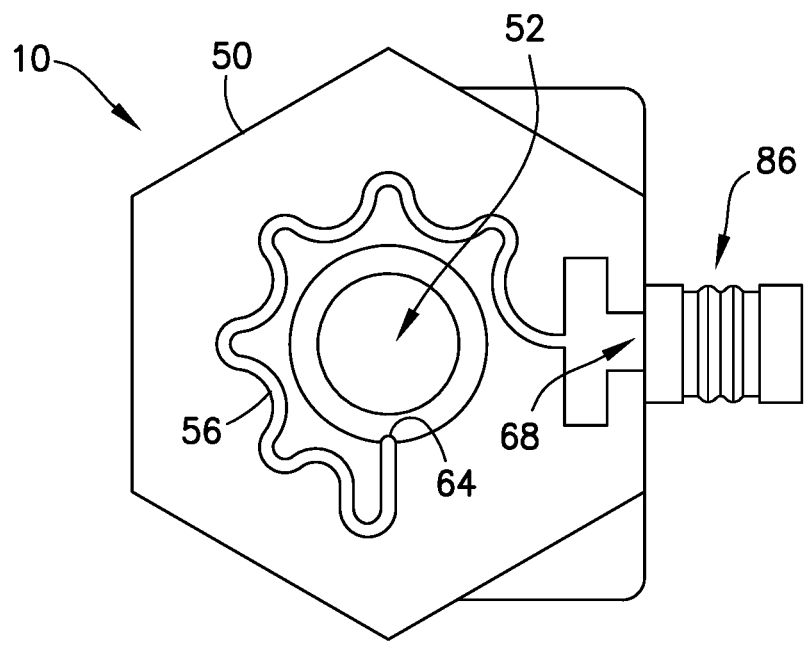
FIG. 7 is a cross-sectional, top view of a biological fluid sampling transfer device in accordance with an embodiment of the present invention.

Referring to FIG. 7, the inlet port 52 is in fluid communication with the transfer port 54 via the mixing channel 56. The inlet port 52 may also include a resealable septum that is transitionable between a closed position and an open position. With the septum in an open position, a blood sample 12 may flow through the inlet port 52 to the mixing channel 56.

The blood sampling transfer device 10 also includes a layer of sample stabilizer 64. The sample stabilizer can be an anticoagulant, or a substance designed to preserve a specific element within the blood such as, for example, RNA, protein analyte, or other element. In one embodiment, the layer of sample stabilizer 64 may be disposed over the blood separation element 58. In one embodiment, a portion of the mixing channel 56 includes the sample stabilizer 64. In other embodiments, the layer of sample stabilizer 64 may be located anywhere between the inlet port 52 and the blood separation element 58. In this manner, as a blood sample 12 flows through the inlet port 52 and into the mixing channel 56, the blood sampling transfer device 10 provides passive and fast mixing of the blood sample 12 with the sample stabilizer 64.

Figure 11:
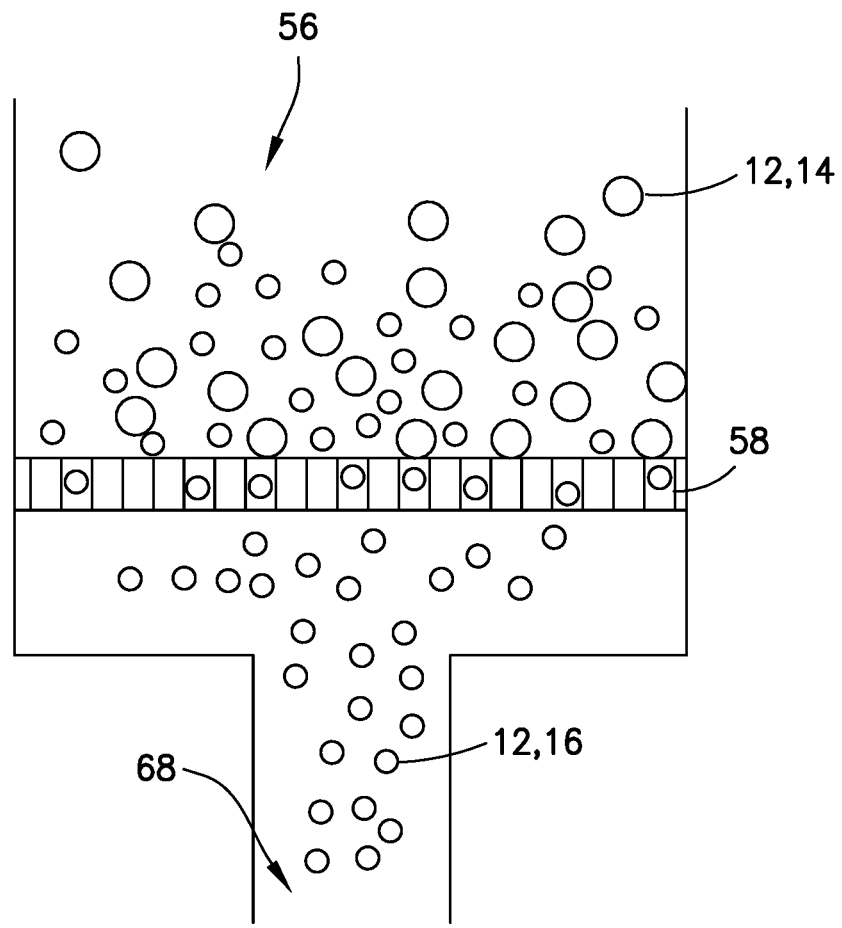
FIG. 11 is a schematic representation of a blood separation element of a biological fluid sampling transfer device in accordance with an embodiment of the present invention.

The blood sampling transfer device 10 includes a blood separation element 58 disposed between the inlet port 52 and the transfer port 54. The blood separation element 58 is adapted to trap the cellular portion 14 of the blood sample 12 within the mixing channel 56 and allow the plasma portion 16 of the blood sample 12 to pass through the blood separation element 58 to the exit channel 68 as shown in FIG. 11.

In one embodiment, the blood separation element 58 may be either hollow fiber membrane filters commercially available, or flat membrane filters, such as track-etch filters commercially available. Membrane filter pore size and porosity can be chosen to optimize separation of clean (i.e., red blood cell free, white blood cell free, and platelet free) plasma in an efficient manner. In another embodiment, the blood separation element 58 includes a lateral flow membrane. In other embodiments, the blood separation element 58 may comprise any filter that is able to trap the cellular portion 14 of the blood sample 12 within the mixing channel 56 and allow the plasma portion 16 of the blood sample 12 to pass through the blood separation element 58 to the exit channel 68.

Figure 6:
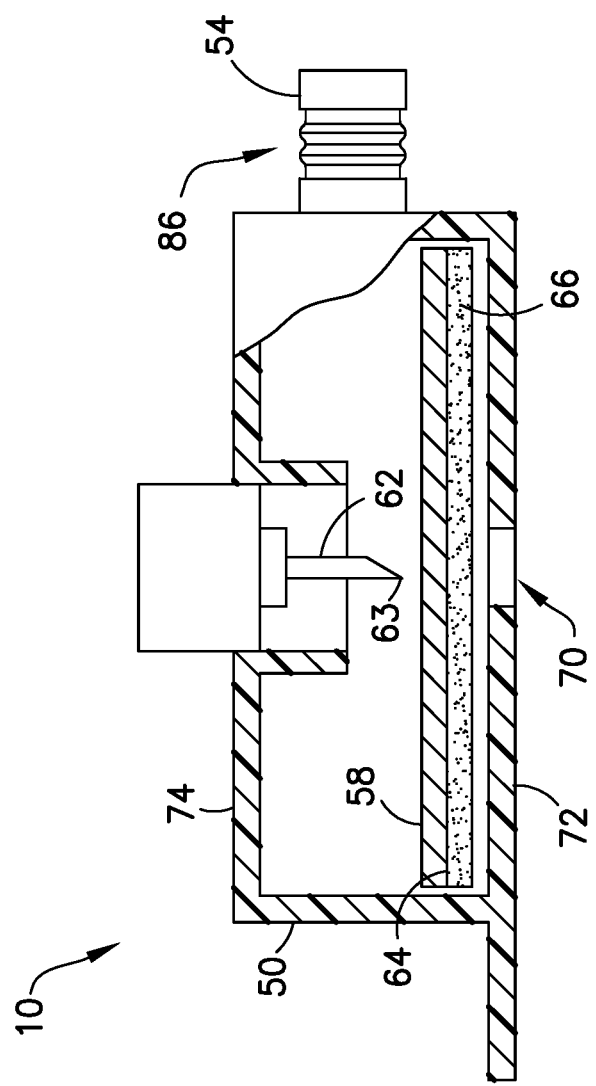
FIG. 6 is a cross-sectional view of the biological fluid sampling transfer device of FIG. 1 in accordance with an embodiment of the present invention.

Referring to FIG. 6, in one embodiment, the blood sampling transfer device 10 includes an integral micro-needle device or lancet device 62. The blood sampling transfer device 10 includes a bottom surface 72 defining an opening 70 and a top surface 74. The integral micro-needle device 62 may be positioned adjacent the top surface 74. The lancet or micro-needle device 62 includes a puncturing element 63 and is adapted for movement between a pre-actuated position wherein the puncturing element 63 is retained within the housing 50 and a puncturing position wherein at least a portion of the puncturing element 63 extends through the opening 70 of the housing 50. In such an embodiment, the blood sampling transfer device 10 includes a wicking membrane 66 adapted to pull the blood sample through the opening 70 into the blood sampling transfer device 10 after the skin of a patient is punctured by the lancet or micro-needle device 62.

In one embodiment, the bottom surface 72 of the housing 50 includes an adhesive. In such an embodiment, the bottom surface 72 includes an adhesive so that the blood sampling transfer device 10 can be secured onto a skin surface of a patient where a blood sample will be accessed using the lancet or micro-needle device 62. In one embodiment, the adhesive of the bottom surface 72 is protected by a peel-off layer, similar to an adhesive bandage, which would be removed before placing the blood sampling transfer device 10 on the skin surface of the patient's body. A hydrogel or other layer (not shown) could be included to provide some thickness to the bottom surface 72 and help improve the stability of the adhesive seal. Additionally, in one embodiment, the adhesive could include a chemistry to create a more liquid-tight seal, similar to painter's tape technology, where wetting from the paint itself causes a chemical reaction with the adhesive to create a more water-tight barrier to prevent the paint from seeping under the tape. In certain cases, the blood sample collected on a top surface of the adhesive tape may be of better quality than blood samples collected by use of a typical lancet by minimizing contact with the skin surface.

Referring to FIG. 7, in one embodiment, the mixing channel 56 comprises a serpentine or spiral shape to promote efficient mixing of a blood sample having a cellular portion and a plasma portion. In other embodiments, the mixing channel 56 comprises other shapes to promote efficient mixing of a blood sample.

Referring to FIG. 8, a blood testing device or point-of-care testing device 22 includes a receiving port 24 adapted to receive the transfer port 54 of the blood sampling transfer device 10. The blood testing device 22 is adapted to receive the transfer port 54 of the blood sampling transfer device 10 for closed transfer of a portion of the plasma portion 16 (FIG. 11) from the exit channel 68 of the blood sampling transfer device 10 to the blood testing device 22. The blood testing device 22 is adapted to receive the plasma portion 16 to analyze the blood sample and obtain test results.

As discussed above, the transfer port 54 of the blood sampling transfer device 10 may include a valve or septum 86 that is transitionable between a closed position and an open position. With the valve or septum 86 in an open position (FIG. 10), the plasma portion 16 of the blood sample 12 may flow through the transfer port 54 to a blood testing device or a point-of-care testing device 22.

Figure 10:
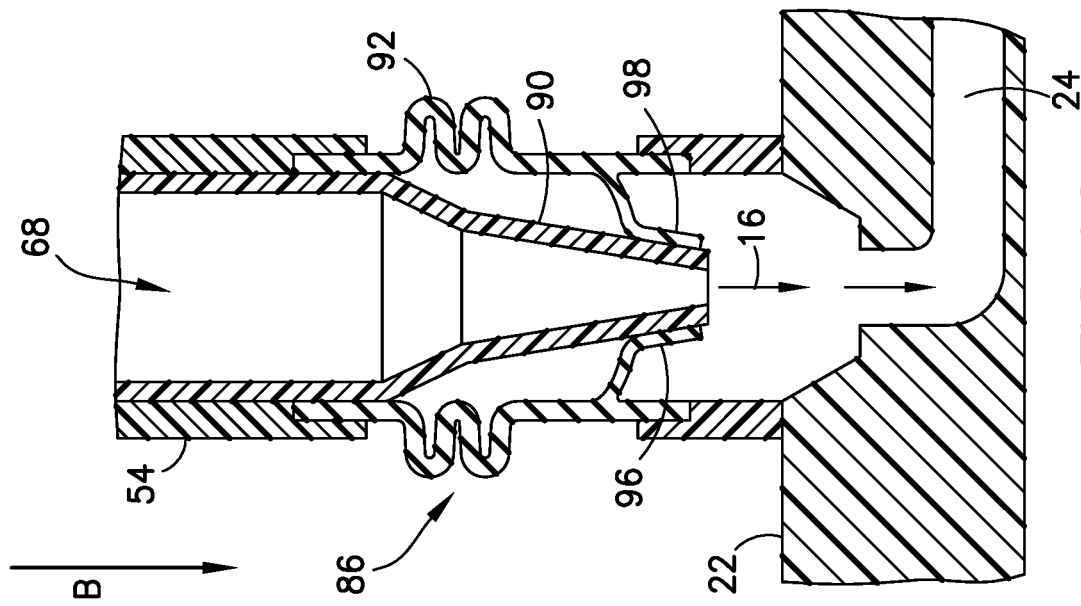
FIG. 10 is a cross-sectional view of a septum of a biological fluid sampling transfer device in accordance with an embodiment of the present invention, with the septum in an open position.
Figure 9:
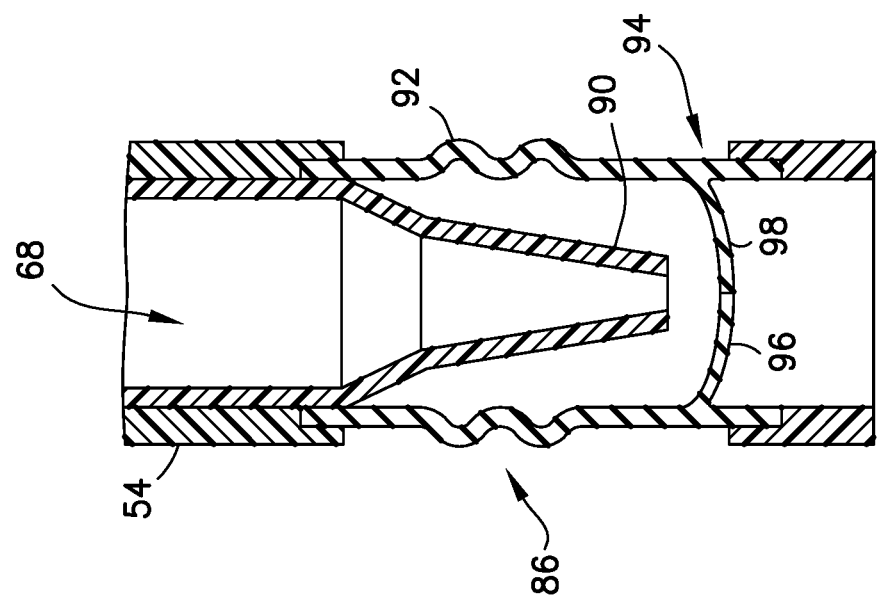
FIG. 9 is a cross-sectional view of a septum of a biological fluid sampling transfer device in accordance with an embodiment of the present invention, with the septum in a closed position.

In one embodiment, referring to FIGS. 9 and 10, the valve 86 may generally include a transfer channel 90, a bellows or deformable wall member 92, and a septum or barrier 94 having a first barrier wall 96 and a second barrier wall 98. Referring to FIG. 9, the valve 86 is in a closed position to prevent the plasma portion 16 of the blood sample 12 from flowing through the transfer port 54. In this manner, the plasma portion 16 is sealed within the blood sampling transfer device 10. Referring to FIG. 10, the valve 86 is in an open position so that the plasma portion 16 of the blood sample 12 may flow through the transfer port 54 to a blood testing device or a point-of-care testing device 22.

Referring to FIG. 10, with the plasma portion 16 received within the transfer port 54 of the blood sampling transfer device 10, the transfer port 54 of the blood sampling transfer device 10 is then positioned over the receiving port 24 of the point-of-care testing device 22. Pushing down in the direction of arrow B compresses the deformable wall member 92 and opens up the first barrier wall 96 and the second barrier wall 98 of the septum 94 as shown in FIG. 10. With the valve 86 in the open position, the plasma portion 16 of the blood sample 12 is allowed to flow through the transfer port 54 and the receiving port 24 to the point-of-care testing device 22 in a closed manner, reducing exposure to the clinician and the patient.

The valve 86 of the blood sampling transfer device 10 only opens when the transfer port 54 is pressed upon the receiving port 24 of the point-of-care testing device 22. This releases the isolated plasma portion 16 directly into the receiving port 24 of the point-of-care testing device 22, thus mitigating unnecessary exposure to the patient's blood.

Referring to FIGS. 1-11, use of a blood sampling transfer device of the present disclosure will now be described. Referring to FIGS. 1-6, a user can select one of the ways, sources, or methods that the blood sampling transfer device 10 is able to receive a blood sample. For example, the system of the present disclosure allows the blood sampling transfer device 10 to receive a blood sample from a variety of sources including, but not limited to, an integral micro-needle device or lancet device 62 (FIG. 6), a blood collection set 100 (FIG. 3), an intravenous line or PICC line 104 (FIG. 4), a capillary device or needle device 106 (FIG. 5), or a finger-stick capillary bed (not shown).

Once a desired method or source is selected, the interface connection portion 60 of the blood sampling transfer device 10 allows the first interface 32 or the second interface 34 to be removably connected to the blood sampling transfer device 10 to allow for the collection of a blood sample 12 into the blood sampling transfer device 10. The blood sampling transfer device 10 is designed to be a closed system for blood collection from various collection sites as described above. Once blood enters the blood sampling transfer device 10 from one of the above selected sources, it is mixed with a sample stabilizer as it travels through the microfluidic mixing channel 56 via capillary action. Next, the blood sample 12 travels through the mixing channel 56 and the blood separation element 58 is adapted to trap the cellular portion 14 of the blood sample 12 within the mixing channel 56 and allow the plasma portion 16 of the blood sample 12 to pass through the blood separation element 58 to the exit channel 68 as shown in FIG. 11.

After disconnecting or removing the blood sampling transfer device 10 from the selected source, the blood sampling transfer device 10 may be engaged with a blood testing device 22. The transfer port 54 may be placed over the receiving port 24 of the point-of-care testing device 22 as shown in FIG. 8. The clinician then presses the transfer port 54 against the receiving port 24 of the point-of-care testing device 22 in the direction of arrow B to open the valve 86 (FIG. 10) and to transfer the collected plasma portion 16 to the point-of-care testing device 22 in a closed manner, reducing exposure to the clinician and the patient. The blood testing device 22 is adapted to receive the transfer port 54 of the blood sampling transfer device 10 for closed transfer of a portion of the plasma portion 16 from the blood sampling transfer device 10 to the blood testing device 22. The blood testing device 22 is adapted to receive the plasma portion 16 to analyze the blood sample and obtain test results.

Some of the advantages of the blood sampling transfer device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to the point-of-care testing device 22. The blood sampling transfer device of the present disclosure enables integrated blood collection and plasma creation in a closed system without centrifugation. The clinician may collect and separate the blood sample and then immediately transfer the plasma portion to the point-of-care testing device 22 without further manipulation. This enables collection and transfer of plasma to the point-of-care testing device 22 without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A multi-component blood sample transfer device comprising:
   a housing comprising an outlet transfer port, a top surface, and a bottom surface, wherein the bottom surface defines an inlet opening therethrough, the inlet opening of the housing being in fluid communication with the outlet transfer port;
   a micro-needle device positioned adjacent the top surface of the housing, wherein the micro-needle device comprises a puncturing element that is moveable with respect to the housing, the puncturing element transitionable between a pre-actuated position and a puncturing position, wherein, in the pre-actuated position, the puncturing element of the micro-needle device is completely retained within the housing, and, in the puncturing position, at least a portion of the puncturing element of the micro-needle device extends through the inlet opening of the housing; and
   a blood separation element disposed in the housing between the inlet opening and the outlet transfer port, wherein the blood separation element comprises a porous filter having a porosity sized to restrain the cellular components of the multi-component blood sample and allow the plasma of the multi-component blood sample to pass therethrough.

2. The multi-component blood sample transfer device of claim 1, further comprising a blood sample stabilizer layer disposed between the inlet opening of the housing and the blood separation element.

3. The multi-component blood sample transfer device of claim 2, wherein the blood sample stabilizer layer comprises an anticoagulant.

4. The multi-component blood sample transfer device of claim 1, further comprising a wicking membrane disposed between the inlet opening and the blood separation element, wherein the wicking membrane is positioned to pull the multi-component blood sample through the inlet opening of the housing.

5. The multi-component blood sample transfer device of claim 4, wherein the blood sample stabilizer layer is positioned between the wicking membrane and the blood separation element.

6. The multi-component blood sample transfer device of claim 1, wherein the outlet transfer port comprises one of a valve or septum.

7. The multi-component blood sample transfer device of claim 6, wherein one of the valve or septum is transitionable between a closed position and an open position.

8. The multi-component blood sample transfer device of claim 1, further comprising a mixing channel within the housing, wherein the mixing channel is disposed in the housing between the inlet opening and the blood separation member, and the blood separation member is disposed in the housing between the mixing channel and the outlet transfer port.

9. The multi-component blood sample transfer device of claim 8, wherein the mixing channel is a serpentine shape.

10. The multi-component blood sample transfer device of claim 8, wherein the mixing channel is a spiral shape.

11. The multi-component blood sample transfer device of claim 1, further comprising an adhesive layer formed on an exterior surface of the bottom surface of the housing.

12. The multi-component blood sample transfer device of claim 11, further comprising a peel-off layer provided over, and removable from, the adhesive layer.

* * * * *